US011103570B2

(12) United States Patent
Steigerwald et al.

(10) Patent No.: US 11,103,570 B2
(45) Date of Patent: Aug. 31, 2021

(54) RECOMBINANT MODIFIED VACCINIA VIRUS ANKARA (MVA) FOOT AND MOUTH DISEASE VIRUS (FMDV) VACCINE

(71) Applicant: Bavarian Nordic A/S, Kvistgaard (DK)

(72) Inventors: Robin Steigerwald, Munich (DE); Markus Kalla, Penzberg (DE)

(73) Assignee: Bavarian Nordic A/S, Kvistgaard (DK)

( * ) Notice: Subject to any disclaimer, the term of this patent is extended or adjusted under 35 U.S.C. 154(b) by 0 days.

(21) Appl. No.: 15/737,028

(22) PCT Filed: Jun. 15, 2016

(86) PCT No.: PCT/EP2016/063691
§ 371 (c)(1),
(2) Date: Dec. 15, 2017

(87) PCT Pub. No.: WO2016/202828
PCT Pub. Date: Dec. 22, 2016

(65) Prior Publication Data
US 2018/0185466 A1   Jul. 5, 2018

Related U.S. Application Data

(60) Provisional application No. 62/175,738, filed on Jun. 15, 2015.

(51) Int. Cl.
*A61K 39/12*   (2006.01)
*A61K 9/00*    (2006.01)
*A61K 39/00*   (2006.01)

(52) U.S. Cl.
CPC ............ *A61K 39/12* (2013.01); *A61K 9/0019* (2013.01); *A61K 2039/552* (2013.01);
(Continued)

(58) Field of Classification Search
None
See application file for complete search history.

(56) References Cited

U.S. PATENT DOCUMENTS 7,527,960 B2 * 5/2009 Nordgren ............. A61K 39/135
435/235.1
8,029,800 B2 * 10/2011 Howley ............... C07K 14/005
424/199.1
(Continued)

FOREIGN PATENT DOCUMENTS

| WO | WO 2002/042480 | 5/2002 |
| WO | WO 2003/0978846 | 11/2003 |
| WO | WO 2010/060632 | * 6/2010 |

OTHER PUBLICATIONS

Polacek et al. (Journal of General Virology. 2013; 94: 1249-1258).*
(Continued)

Primary Examiner — Shanon A. Foley

(57) ABSTRACT

The present invention relates to modified poxviral vectors and to methods of making and using the same. In particular, the invention relates to recombinant modified vaccinia virus Ankara-based (MVA-based) vaccine against FMDV infection and to related products, methods and uses. Specifically, the present invention relates to genetically engineered (recombinant) MVA vectors comprising at least one heterologous nucleotide sequence encoding an antigenic determinant of a FMDV protein. The invention also relates to products, methods and uses thereof, e.g., suitable to induce a protective immune response in a subject.

10 Claims, 3 Drawing Sheets

Specification includes a Sequence Listing.

| Lane No. | Sample ID |
|---|---|
| 1 | Input construct #7 (MVA-mBN360B, FDP) |
| 2 | Input MVA-BN, empty vector |
| 3 | Elution - anti-P1 mAb + MVA-mBN360, FDP |
| 4 | Elution - anti-P1 mAb + MVA-BN, empty vector |

Anti VP3 (D12-8) 1:5000   Anti VP2 1:1000
Anti rab-HRP 1:30000       Anti m-HRP 1:50000

Cell line: Hela cells
Infection conditions:
MVA-mBN360B #141, PRQD49A13, FDP
MVA-BN 5PPC MVB17A10
MOI MOI 10; collected 16h p.i.

IP conditions (O/N incubation at 4°C):
Beads: 50uL protein A/G magnetic Beads
Abs: 20ug of P1Ab (10ug per 25uL)
Lysate: four 6-wells per IP were lysed with 1mL of 0.5X lysis buffer
1mL of lysate was used per IP

(52) U.S. Cl.
CPC ........... *C12N 2710/24034* (2013.01); *C12N 2710/24143* (2013.01); *C12N 2770/32134* (2013.01)

(56) References Cited

U.S. PATENT DOCUMENTS

| | | | | |
|---|---|---|---|---|
| 2012/0258133 | A1* | 10/2012 | Charleston | A61P 31/12 424/204.1 |
| 2018/0066235 | A1* | 3/2018 | Puckette | A61K 39/135 |

OTHER PUBLICATIONS

Zunszain et al. (Journal of Molecular Biology. 2010; 395: 375-389).*
Jamal and Belsham (Veterinary Research. 2013; 44: 116: 1-14).*
Haydon et al. (Emerging Infectious Diseases. 2002; 8 (12): 1468-1473).*
Paton et al. (Current Opinion in Virology. 2018; 28: 85-91).*
Wennier et al. (PLoSOne. Aug. 2013; 8 (8): e73511: 1-15).*
Wyatt et al. (Vaccine. 1996; 14(15): 1451-1458).*
Rosel et al. (Journal of Virology. 1986: 60 (2): 436-449).*
Seq alignment of SEQ ID 6 with geneseq db acc No. ABB76724 by King in WO200200251 May 2002.*
Seq alignment of SEQ ID 7 with geneseq db acc No. ABB76724 by King in WO200200251 May 2002.*
Berinstein et al., Protective Immunity against foot and mouth disease virus induced by a recombinant vaccinia virus, Vaccine 18: 2231-2238 (2000).
Grubman et al., Prospects, including time-frames, for improved foot and mouth disease vaccines, Rev. sci. tech Off. Int. Epiz., 21: 589-600 (2002).
Polacek et al., Low levels of foot-and-mouth disease virus 3C protease expression are required to achieve optimal capsid protein expression and processing mammalian cells, J. of General Virology, 94: 1249-1258 (2013).
Sweeney et al., Structural and Mutagenic Analysis of Foot-and-Mouth Disease virus 3c Protease Reveals the Roel for the Beta-Ribbon in Proteolysis, Journal of Virology, 81:115-124 (2007).
Written Opinion and Search Report of the International Search Authority for PCT/EP2016/063691 dated Sep. 9, 2016.
Boyle et al., "Genetic Confirmation that the H5 Protein is Required for Vaccinia Virus DNA Replication," J. Virol., 2015, pp. 6312-6327, vol. 89.
Meisinger-Henschel et al., "Genomic sequence of chorioallantois vaccinia virus Ankara, the ancestor of modified vaccinia virus Ankara," J. Gen. Virol., 2007, pp. 3249-3259, vol. 88, and supplemental table.
Porta et al., "Efficient production of foot-and-mouth disease virus empty capsids in insect cells following down regulation of 3C protease activity," J. Virol. Meth., 2013, pp. 406-412, vol. 187.
Steigerwald et al., "Evaluation of modified Vaccinia Ankara-based vaccines against foot-and-mouth disease serotype A24 in cattle," Vaccine, 2020, pp. 769-778, vol. 38.

* cited by examiner

SEQUENCE LISTING

<160> NUMBER OF SEQ ID NOS: 7

<210> SEQ ID NO 1
<211> LENGTH: 40
<212> TYPE: DNA
<213> ORGANISM: Artificial sequence
<220> FEATURE:
<223> OTHER INFORMATION: Synthetic promoter

<400> SEQUENCE: 1
aaaaattgaa attttatttt ttttttttgg aatataaata                          40

<210> SEQ ID NO 2
<211> LENGTH: 234
<212> TYPE: DNA
<213> ORGANISM: Artificial sequence
<220> FEATURE:
<223> OTHER INFORMATION: Synthetic promoter

<400> SEQUENCE: 2
aaaaattgaa attttatttt ttttttttgg aatataaata aaaaattgaa aaactattct    60
aatttattgc acggtccggt aaaaattgaa aaactattct aatttattgc acggtccggt   120
aaaaattgaa aaactattct aatttattgc acggtccggt aaaaattgaa aaactattct   180
aatttattgc acggtccggt aaaaattgaa aaactattct aatttattgc acgg         234

<210> SEQ ID NO 3
<211> LENGTH: 104
<212> TYPE: DNA
<213> ORGANISM: Artificial sequence
<220> FEATURE:
<223> OTHER INFORMATION: Synthetic promoter

<400> SEQUENCE: 3
tccaaaccca cccgcttttt atagtaagtt tttcacccat aaataataaa tacaataatt    60
aatttctcgt aaaagtagaa aatatattct aatttattgc acgg                    104

<210> SEQ ID NO 4
<211> LENGTH: 227
<212> TYPE: DNA
<213> ORGANISM: Artificial sequence
<220> FEATURE:
<223> OTHER INFORMATION: Synthetic promoter

<400> SEQUENCE: 4
gttttgaaaa ttttttttata ataaatatcc ggtaaaaatt gaaaaactat tctaatttat   60
tgcacggtcc ggtaaaaatt gaaaaactat tctaatttat tgcacggtcc ggtaaaaatt  120
gaaaaactat tctaatttat tgcacggtcc ggtaaaaatt gaaaaactat tctaatttat  180
tgcacggtcc ggtaaaaatt gaaaaactat tctaatttat tgcacgg                227

<210> SEQ ID NO 5
<211> LENGTH: 124
<212> TYPE: DNA
<213> ORGANISM: Artificial sequence
<220> FEATURE:
<223> OTHER INFORMATION: Synthetic promoter

<400> SEQUENCE: 5
taaaaataga aactataatc atataatagt gtaggttggt agtattgctc ttgtgactag    60
agactttagt taaggtactg taaaaataga aactataatc atataatagt gtaggttggt   120
agta                                                                124

<210> SEQ ID NO 6
<211> LENGTH: 737
<212> TYPE: PRT
<213> ORGANISM: Foot-and-mouth disease virus

<400> SEQUENCE: 6

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Ser Thr Gln Leu Gly Asp Asn Thr Ile Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Thr Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ser Thr Glu Glu Asp His
        115                 120                 125

Val Ala Gly Pro Asn Thr Ser Gly Leu Glu Thr Arg Val Val Gln Ala
    130                 135                 140

Glu Arg Phe Phe Lys Lys Phe Leu Phe Asp Trp Thr Thr Asp Lys Pro
145                 150                 155                 160

Phe Gly Tyr Leu Thr Lys Leu Glu Leu Pro Thr Asp His His Gly Val
                165                 170                 175

Phe Gly His Leu Val Asp Ser Tyr Ala Tyr Met Arg Asn Gly Trp Asp
            180                 185                 190

Val Glu Val Ser Ala Val Gly Asn Gln Phe Asn Gly Gly Cys Leu Leu
        195                 200                 205

Val Ala Met Val Pro Glu Trp Lys Ala Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
                245                 250                 255

Tyr Lys Lys His Lys Pro Trp Thr Leu Val Val Met Val Leu Ser Pro
            260                 265                 270

Leu Thr Val Ser Asn Thr Ala Ala Pro Gln Ile Lys Val Tyr Ala Asn
        275                 280                 285

Ile Ala Pro Thr Tyr Val His Val Ala Gly Glu Leu Pro Ser Lys Glu
    290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Val Tyr Gly Lys Val Tyr Asn Pro
                325                 330                 335

Pro Lys Thr Asn Tyr Pro Gly Arg Phe Thr Asn Leu Leu Asp Val Ala
            340                 345                 350

Glu Ala Cys Pro Thr Phe Leu Arg Phe Asp Asp Gly Lys Pro Tyr Val
        355                 360                 365

Val Thr Arg Ala Asp Asp Thr Arg Leu Leu Ala Lys Phe Asp Val Ser

```
    370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
                405                 410                 415

Gly Ser Thr Asp Ser Lys Ala Arg Tyr Met Val Ala Tyr Ile Pro Pro
            420                 425                 430

Gly Val Glu Thr Pro Pro Asp Thr Pro Glu Glu Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Thr Asn Val Gln Gly Trp Val Cys Val Tyr Gln Ile Thr His
                485                 490                 495

Gly Lys Ala Glu Asn Asp Thr Leu Leu Val Ser Ala Ser Ala Gly Lys
            500                 505                 510

Asp Phe Glu Leu Arg Leu Pro Ile Asp Pro Arg Thr Gln Thr Thr Thr
        515                 520                 525

Thr Gly Glu Ser Ala Asp Pro Val Thr Thr Thr Val Glu Asn Tyr Gly
    530                 535                 540

Gly Asp Thr Gln Val Gln Arg Arg His His Thr Asp Val Gly Phe Ile
545                 550                 555                 560

Met Asp Arg Phe Val Lys Ile Asn Ser Leu Ser Pro Thr His Val Ile
                565                 570                 575

Asp Leu Met Gln Thr His Lys His Gly Ile Val Gly Ala Leu Leu Arg
            580                 585                 590

Ala Ala Thr Tyr Tyr Phe Ser Asp Leu Glu Ile Val Val Arg His Asp
        595                 600                 605

Gly Asn Leu Thr Trp Val Pro Asn Gly Ala Pro Glu Ala Ala Leu Ser
    610                 615                 620

Asn Thr Ser Asn Pro Thr Ala Tyr Asn Lys Ala Pro Phe Thr Arg Leu
625                 630                 635                 640

Ala Leu Pro Tyr Thr Ala Pro His Arg Val Leu Ala Thr Val Tyr Asp
                645                 650                 655

Gly Thr Asn Lys Tyr Ser Ala Ser Asp Ser Arg Ser Gly Asp Leu Gly
            660                 665                 670

Ser Ile Ala Ala Arg Val Ala Thr Gln Leu Pro Ala Ser Phe Asn Tyr
        675                 680                 685

Gly Ala Ile Gln Ala Gln Ala Ile His Glu Leu Leu Val Arg Met Lys
    690                 695                 700

Arg Ala Glu Leu Tyr Cys Pro Arg Pro Leu Leu Ala Ile Lys Val Thr
705                 710                 715                 720

Ser Gln Asp Arg Tyr Lys Gln Lys Ile Ile Ala Pro Ala Lys Gln Leu
                725                 730                 735

Leu

<210> SEQ ID NO 7
<211> LENGTH: 214
<212> TYPE: PRT
<213> ORGANISM: Foot-and-mouth disease virus

<400> SEQUENCE: 7

Ser Gly Ala Pro Pro Thr Asp Leu Gln Lys Met Val Met Gly Asn Thr
```

```
1               5                   10                  15
Lys Pro Val Glu Leu Asn Leu Asp Gly Lys Thr Val Ala Ile Cys Cys
            20                  25                  30

Ala Thr Gly Val Phe Gly Thr Ala Tyr Leu Val Pro Arg His Leu Phe
            35                  40                  45

Ala Glu Lys Tyr Asp Lys Ile Met Leu Asp Gly Arg Ala Met Thr Asp
        50                  55                  60

Ser Asp Tyr Arg Val Phe Glu Phe Glu Ile Lys Val Lys Arg Thr Gly
65                  70                  75                  80

His Ala Leu Arg Arg Gly Thr His Trp Leu Leu His Arg Gly Asn Cys
                85                  90                  95

Val Arg Asp Ile Thr Lys His Phe Arg Asp Thr Ala Arg Met Lys Lys
                100                 105                 110

Gly Thr Pro Val Val Gly Val Val Asn Asn Ala Asp Val Gly Arg Leu
            115                 120                 125

Ile Phe Ser Gly Glu Ala Leu Thr Tyr Lys Asp Ile Val Val Cys Met
            130                 135                 140

Asp Gly Asp Thr Met Pro Gly Leu Phe Ala Tyr Lys Ala Ala Thr Arg
145                 150                 155                 160

Ala Gly Tyr Cys Gly Gly Ala Val Leu Ala Lys Asp Gly Ala Asp Thr
                165                 170                 175

Phe Ile Val Gly Thr His Ser Ala Gly Gly Asn Gly Val Gly Tyr Cys
            180                 185                 190

Ser Cys Val Ser Arg Ser Met Leu Gln Lys Met Lys Ala His Val Asp
            195                 200                 205

Pro Glu Pro His His Glu
            210
```

RECOMBINANT MODIFIED VACCINIA VIRUS ANKARA (MVA) FOOT AND MOUTH DISEASE VIRUS (FMDV) VACCINE

This application is a National Phase application under 35 U.S.C. § 371 of International Application No. PCT/EP2016/063691, filed Jun. 15, 2016, and claims the benefit under 35 U.S.C. § 119 (e) U.S. Provisional Patent Application 62/175,738 filed Jun. 15, 2015, the disclosures of which are incorporated by reference herein in their entirety.

This invention was made with Government support under HSHQDC-12-C-00051 awarded by U.S. Dept. of Homeland Security Office of Procurement and Operations. The Government has certain rights in the invention.

FIELD OF THE INVENTION

The present invention relates to an improved FMDV vaccine comprising a recombinant modified vaccinia virus Ankara-based (MVA-based) vaccine against FMDV infection and to related products, methods and uses. Specifically, the present invention relates to genetically engineered (recombinant) MVA vectors comprising a heterologous nucleotide sequence encoding an antigenic determinant of a FMDV protein. The invention also relates to products, methods and uses thereof, e.g., suitable to induce a protective immune response in a subject.

BACKGROUND OF THE INVENTION

Foot-and-mouth disease (FMD) is one of the most virulent and contagious diseases affecting farm animals. This disease is endemic in numerous countries in the world, especially in Africa, Asia and South America. In addition, epidemic outbreaks can occur periodically. The presence of this disease in a country may have very severe economic consequences resulting from loss of productivity, loss of weight and milk production in infected herds, and from trade embargoes imposed on these countries. The measures taken against this disease consist of strict application of import restrictions, hygiene controls and quarantine, slaughtering sick animals and vaccination programs using inactivated vaccines, either as a preventive measure at the national or regional level, or periodically when an epidemic outbreak occurs.

FMD is characterized by its short incubation period, its highly contagious nature, the formation of ulcers in the mouth and on the feet and sometimes, the death of young animals. FMD affects a number of animal species, in particular cattle, pigs, sheep and goats. The agent responsible for this disease is a ribonucleic acid (RNA) virus belonging to the Aphthovirus genus of the Picornaviridae family (Cooper et al., Intervirology, 1978, 10, 165-180). At present, at least seven types of foot-and-mouth disease virus (FMDV) are known: the European types (A, O and C), the African types (SAT1, SAT2 and SAT3) and an Asiatic type (Asia 1). Numerous sub-types have also been distinguished (Kleid et al. Science (1981), 214, 1 125-1 129).

FMDV is a naked icosahedral virus of about 25 nm in diameter, containing a single-stranded RNA molecule consisting of about 8500 nucleotides, with a positive polarity. This RNA molecule comprises a single open reading frame (ORF), encoding a single polyprotein containing, inter alia, the capsid precursor also known as protein P1 or P88. The protein P1 is myristylated at its amino-terminal end. During the maturation process, the protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, the protein VP0 is then cleaved into two proteins, VP4 and VP2 (or 1A and 1B respectively). The mechanism for the conversion of the proteins VP0 into VP2 and VP4, and for the formation of mature virions is not known. The proteins VP1, VP2 and VP3 have a molecular weight of about 26,000 Da, while the protein VP4 is smaller at about 8,000 Da.

The simple combination of the capsid proteins forms the protomer or 5S molecule, which is the elementary constituent of the FMDV capsid. This protomer is then complexed into a pentamer to form the 12S molecule. The virion results from the encapsidation of a genomic RNA molecule by assembly of twelve 12S pentamers, thus constituting the 146S particles. The viral capsid may also be formed without the presence of an RNA molecule inside it (hereinafter "empty capsid"). The empty capsid is also designated as particle 70S. The formation of empty capsids may occur naturally during viral replication or may be produced artificially by chemical treatment.

Many hypotheses, research routes, and proposals have been developed in an attempt to design effective vaccines against FMD. Currently, the only vaccines on the market comprise inactivated virus. Concerns about safety of the FMDV vaccine exist, as outbreaks of FMD in Europe have been associated with shortcomings in vaccine manufacture (King, A. M. Q. et al, (1981) Nature 293: 479-480). The inactivated vaccines do not confer long-term immunity, thus requiring booster injections given every year, or more often in the event of epidemic outbreaks. In addition, there are risks linked to incomplete inactivation and/or to the escape of virus during the production of inactivated vaccines (King, A. M. Q., ibid). A goal in the art has been to construct conformationally correct immunogens lacking the infective FMDV genome to make effective and safe vaccines.

Vaccinia virus has been used successfully to immunize against smallpox, culminating in the worldwide eradication of smallpox in 1980. Thus, a new role for poxviruses became important, that of a genetically engineered vector for the expression of foreign genes (Panicali and Paoletti, 1982; Paoletti et al, 1984). Genes encoding heterologous antigens have been expressed in vaccinia, often resulting in protective immunity against challenge by the corresponding pathogen (reviewed in Tartaglia et al., 1990). A highly attenuated strain of vaccines, designated MVA, has also been used as a vector for poxvirus-based vaccines. Use of MVA is described in U.S. Pat. No. 5,185,146.

The excellent safety profile of MVA, because of its replication deficiency in human cells, has been proven in many clinical trials, including vaccination of immune-compromised individuals, and during the smallpox eradication campaign in the 1970s, when 120,000 people were vaccinated with MVA (A. Mayr et al., "The smallpox vaccination strain MVA: marker, genetic structure, experience gained with the parenteral vaccination and behavior in organisms with a debilitated defense mechanism," *Zentralbl. Bakteriol. B* 167(5-6):375-390 (1978)). Since then many different recombinant MVA vaccines have been generated and tested for the ability to immunize animals and humans against infectious (e.g., HIV, malaria) and non-infectious (e.g., prostate cancer) diseases. Its proven safety and good immunogenicity thus make MVA a prime candidate for a T- and B-cell-inducing vaccine vector.

Additional vaccine vector systems involve the use of avipox viruses, which are naturally host-restricted poxviruses. Both fowlpoxvirus (FPV; Taylor et al. 1988a, b) and canarypoxvirus (CPV; Taylor et al., 1991 & 1992) have been engineered to express foreign gene products. Fowlpox virus (FPV) is the prototypic virus of the Avipox genus of the Poxvirus family. The virus causes an economically important disease of poultry that has been well controlled since the 1920's by the use of live attenuated vaccines. Replication of the avipox viruses is limited to avian species (Matthews, 1982) and there are no reports in the literature of avipox virus causing a productive infection in any non-avian species including man. This host restriction provides an inherent safety barrier against transmission of the virus to other species and makes the use of avipox virus based vaccine vectors in veterinary and human applications an attractive proposition.

Other attenuated poxvirus vectors have been prepared by genetic modifications of wild type strains of virus. The NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen. Another engineered poxvirus vector is ALVAC, derived from canarypox virus (see U.S. Pat. No. 5,756,103). ALVAC does not productively replicate in non-avian hosts, a characteristic thought to improve its safety profile (Taylor et al., 1991 & 1992). ALVAC was deposited under the terms of the Budapest Treaty with the American Type Culture Collection under accession number VR-2547. Yet another engineered poxvirus vector is TRO-VAC, derived from fowlpox virus (see U.S. Pat. No. 5,766,599).

Recombinant poxviruses can be constructed in two steps known in the art and analogous to the methods for creating synthetic recombinants of poxviruses such as the vaccinia virus and avipox virus described in U.S. Pat. Nos. 4,769,330; 4,722,848; 4,603, 112; 5, 110,587; 5, 174,993; 5,494,807; and 5,505,941, the disclosures of which are incorporated herein by reference. It can thus be appreciated that provision of an FMDV recombinant poxvirus, and of compositions and products therefrom, particularly ALVAC or TROVAC-based FMDV recombinants and compositions and products therefrom, especially such recombinants containing the P1 genes and/or 3C protease gene of FMDV, and compositions and products therefrom, would be a highly desirable advance over the current state of technology.

Considering the susceptibility of animals (including humans, albeit rarely), to FMDV, a method of preventing FMDV infection and protecting animals is essential. Accordingly, there is a need for an effective vaccine against FMDV.

BRIEF SUMMARY OF THE INVENTION

It is determined in the present invention that various prime-boost combinations of replication deficient and/or replication incompetent vectors generate effective immune protection against FMDV infection.

Accordingly, one aspect of the present invention provides a recombinant MVA comprising a nucleotide sequence encoding an antigenic determinant of at least one foot-and-mouth disease virus (FMDV) antigens. In a preferred embodiment, the MVA is MVA-BN.

Advantageously, the FMDV antigen(s) can be VP1, VP2, VP3, VP4, 2A, 2B and 3C. Advantageously, the nucleic acid molecule encoding one or more foot-and-mouth disease virus (FMDV) antigen(s) is a cDNA encoding FMDV P1 region and a cDNA encoding FMDV 3C protease of FMDV.

In one embodiment, the FMDV antigens are operably linked to a promoter sequence, e.g. the PrMVA095R or Pr13.5-long promoter.

A further aspect of the invention relates to a composition comprising the MVA and a pharmaceutical or veterinary acceptable carrier, excipients, or vehicle.

A further aspect of the invention relates to a method of eliciting an immune response to FMDV in a subject, comprising administering the MVA of the present invention to the subject.

A further aspect of the invention relates to a method of treatment and/or prevention of a FMDV caused disease in a subject.

In a further aspect the invention relates to a vaccine and cell comprising the MVA of the present invention.

A further aspect of the invention relates to a kit comprising the recombinant MVA of the invention and/or the composition of the invention in a first vial or container for a first administration (priming) and in a second vial or container for a second administration (boosting).

In yet another aspect of the present invention, a method of producing a recombinant MVA of the invention or the antigenic determinant expressed from the genome of said MVA.

These and other objects of the invention will be described in further detail in connection with the detailed description of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
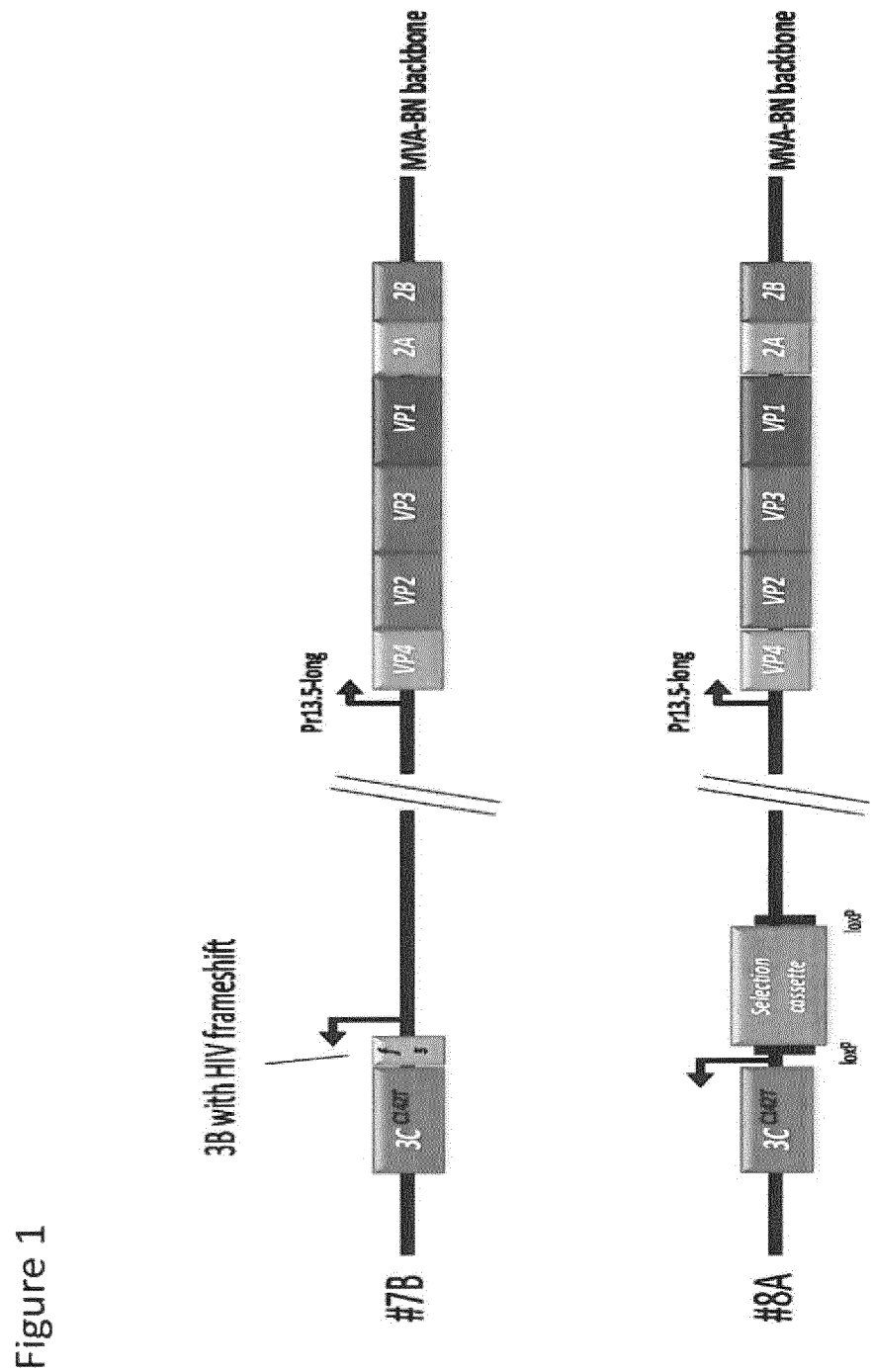
FIG. 1 shows schematic presentation of two exemplary constructs: #7B (MVA-mBN360B) and #8A MVA-mBN361A).

The present inventors have determined that a vaccine comprising a recombinant modified vaccinia virus Ankara (MVA) comprising a heterologous nucleotide sequence encoding an antigenic determinant of a FMDV provides a FMDV vaccine capable of inducing both cellular and humoral responses sufficient to confer protective immunity to FMDV.

In one aspect, the present invention relates to a modified recombinant MVA virus expressing at least one nucleic acid sequences encoding for one or more FMDV antigens. The viral vector according to the present invention is preferably an MVA virus, such as MVA-BN. The modified recombinant vector comprises a heterologous nucleic acid sequence, which encodes an antigenic protein, e.g., derived from FMDV ORFs that are encoded by the P1 (comprising VP1, VP2, VP3, VP4, and 2A), 2B, and/or 3C regions.

In another aspect, the present invention relates to a modified recombinant MVA virus that includes, in a non-essential region of the virus genome, at least one heterologous nucleic acid sequence that encodes one or more antigens from FMDV, such as gene products of the P1 gene (comprising VP1, VP2, VP3, VP4, 2A), 2B, and/or 3C.

In a still further aspect, the present invention relates to methods of eliciting an immune response to FMDV in a subject, comprising administering the recombinant MVA vector of the present invention. The present invention also relates to methods of eliciting an immune response to FMDV in a subject, comprising administering the recombinant MVA virus of the present invention.

In one aspect, the present invention relates to recombinant MVA viruses containing at least one nucleic acid sequence expressing one or more antigens from FMDV, advantageously in a non-essential region of the MVA virus genome. The MVA virus can be an attenuated MVA virus such as MVA-BN.

According to the present invention, the recombinant MVA viral vectors express at least one nucleic acid sequence encoding one or more FMDV antigens. In particular, any or all genes or open reading frames (ORFs) encoding FMDV antigens can be isolated, characterized and inserted into MVA recombinants. The resulting recombinant MVA virus is used to infect an animal. Expression in the animal of FMDV antigens results in an immune response in the animal to FMDV. Thus, the recombinant MVA virus of the present invention may be used in an immunological composition or vaccine to provide a means to induce an immune response, which may, but need not be, protective. The molecular biology techniques used are described by Sambrook et ah (1969).

The invention also contemplates FMDV antigens that can be delivered as a naked DNA plasmid or vector, or DNA vaccine or immunological or immunogenic compositions comprising nucleic acid molecules encoding and expressing in vivo an FMDV antigen(s).

The FMDV antigen of interest can be obtained from FMDV or can be obtained from in vitro and/or in vivo recombinant expression of FMDV gene(s) or portions thereof. The FMDV antigen of interest can also be provided using synthetic FMDV sequences. The FMDV antigen of interest can be, but are not limited to: U, Lab, P1-2 A (comprising VP1, VP2, VP3, VP4, and 2A); P2 (comprising 2B and 2C), and P3 (comprising 3A, 3B, VPg, 3C, and 3D), or portions thereof. In a preferred embodiment, the FMDV antigens are P1 and 3C. In a particularly preferred embodiment, the FMDV antigens are P1-2A or P1-2A, 2B. Reference is made herein to U.S. patent application Ser. No. 10/327,481, issued as U.S. Pat. No. 7,531,182, relating to isolation of FMDV genome sequences, the contents of which are incorporated by reference, herein. An exemplary P1 amino acid sequence of FMDV strain A10 is set forth in SEQ ID NO:6, and an exemplary 3C amino acid sequence of FMDV strain A10 is set forth in SEQ ID NO:7.

Reference will now be made in detail to exemplary embodiments of the invention, examples of which are illustrated in the accompanying drawings.

In one aspect, the present invention provides a recombinant modified vaccinia virus Ankara (MVA) comprising a nucleotide sequence encoding an antigenic determinant of a FMDV. In another aspect, the present invention provides a recombinant MVA vector comprising a heterologous nucleotide sequence encoding an antigenic determinant of a FMDV.

MVA has been generated by more than 570 serial passages on chicken embryo fibroblasts of the dermal vaccinia strain Ankara [Chorioallantois vaccinia virus Ankara virus, CVA; for review see Mayr et al. (1975), *Infection* 3, 6-14] that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [Mayr et al. (1975)]. It was shown in a variety of animal models that the resulting MVA was avirulent [Mayr, A. & Danner, K. (1978), *Dev. Biol. Stand.* 41: 225-234]. As part of the early development of MVA as a pre-smallpox vaccine, there were clinical trials using MVA-517 in combination with Lister Elstree [Stickl (1974), *Prev. Med.* 3: 97-101; Stickl and Hochstein-Mintzel (1971), *Munch. Med. Wochenschr.* 113: 1149-1153] in subjects at risk for adverse reactions from vaccinia. In 1976, MVA derived from MVA-571 seed stock (corresponding to the 571' passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteriol.* (B) 167: 375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies. MVA-575 was deposited on Dec. 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells [Blanchard et al. (1998), *J. Gen. Virol.* 79:1159-1167; Carroll & Moss (1997), *Virology* 238:198-211; U.S. Pat. No. 5,185,146; Ambrosini et al. (1999), *J. Neurosci. Res.* 55: 569]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN. A representative sample of MVA-BN was deposited on Aug. 30, 2000 at the European Collection of Cell Cultures (ECACC), Health Protection Agency, Porton Down, Salisbury, Wiltshire SP4 0JG, United Kingdom, under Accession No. V00083008. MVA-BN is further described in WO 02/42480 (US 2003/0206926) and WO 03/048184 (US 2006/0159699), both of which are incorporated by reference herein.

MVA-BN can attach to and enter human cells where virally-encoded genes are expressed very efficiently. MVA-BN is strongly adapted to primary chicken embryo fibroblast (CEF) cells and does not replicate in human cells. In human cells, viral genes are expressed, and no infectious virus is produced. MVA-BN is classified as Biosafety Level 1 organism according to the Centers for Disease Control and Prevention in the United States. Preparations of MVA-BN and derivatives have been administered to many types of animals, and to more than 2000 human subjects, including immune-deficient individuals. All vaccinations have proven to be generally safe and well tolerated. Despite its high attenuation and reduced virulence, in preclinical studies MVA-BN has been shown to elicit both humoral and cellular immune responses to vaccinia and to heterologous gene products encoded by genes cloned into the MVA genome [E. Harrer et al. (2005), *Antivir. Ther.* 10(2):285-300; A. Cosma et al. (2003), *Vaccine* 22(1):21-9; M. Di Nicola et al. (2003), *Hum. Gene Ther.* 14(14):1347-1360; M. Di Nicola et al. (2004), *Clin. Cancer Res.*, 10(16):5381-5390].

"Derivatives" or "variants" of MVA refer to viruses exhibiting essentially the same replication characteristics as MVA as described herein, but exhibiting differences in one or more parts of their genomes. MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [Boukamp et al (1988), *J. Cell Biol.* 106: 761-771], the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably threefold less than MVA-575 in Hela cells and HaCaT cell lines. Tests and assay for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input) referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Preclinical tests have revealed that MVA-BN demonstrates superior attenuation and efficacy compared to other MVA strains (WO 02/42480). An additional property of MVA-BN strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the present invention can be prepared using methods known in the art, such as those described in WO/2002/042480 and WO/2002/24224, both of which are incorporated by reference herein.

In another aspect, an MVA viral strain suitable for generating the recombinant virus may be strain MVA-572, MVA-575 or any similarly attenuated MVA strain. Also suitable may be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

Antigenic Determinants

Any DNA of interest or foreign gene can be inserted as a heterologous nucleotide sequence encoding an antigenic determinant into the viral vectors described herein. Foreign genes for insertion into the genome of a virus in expressible form can be obtained using conventional techniques for isolating a desired gene. For organisms which contain a DNA genome, the genes encoding an antigen of interest can be isolated from the genomic DNA; for organisms with RNA genomes, the desired gene can be isolated from cDNA copies of the genome. The antigenic determinant can also be encoded by a recombinant DNA that is modified based on a naturally occurring sequence, e.g., to optimize the antigenic response, gene expression, etc.

The term "antigenic determinant" refers to any molecule that stimulates a host's immune system to make an antigen-specific immune response, whether a cellular response or a humoral antibody response. Antigenic determinants may include proteins, polypeptides, antigenic protein fragments, antigens, and epitopes which still elicit an immune response in a host and form part of an antigen, homologues or variants of proteins, polypeptides, and antigenic protein fragments, antigens and epitopes including, for example, glycosylated proteins, polypeptides, antigenic protein fragments, antigens and epitopes, and nucleotide sequences encoding such molecules. Thus, proteins, polypeptides, antigenic protein fragments, antigens and epitopes are not limited to particular native nucleotide or amino acid sequences but encompass sequences identical to the native sequence as well as modifications to the native sequence, such as deletions, additions, insertions and substitutions.

The term "epitope" refers to a site on an antigen to which B- and/or T-cells respond, either alone or in conjunction with another protein such as, for example, a major histocompatibility complex ("MHC") protein or a T-cell receptor. Epitopes can be formed both from contiguous amino acids or noncontiguous amino acids juxtaposed by secondary and/or tertiary folding of a protein. Epitopes formed from contiguous amino acids are typically retained on exposure to denaturing solvents, while epitopes formed by tertiary folding are typically lost on treatment with denaturing solvents. An epitope typically includes at least 5, 6, 7, 8, 9, 10 or more amino acids—but generally less than 20 amino acids—in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996).

Preferably, a homologue or variant has at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% identity with the referenced protein, polypeptide, antigenic protein fragment, antigen and epitope at the level of nucleotide or amino acid sequence.

Techniques for determining sequence identity between nucleic acids and amino acids are known in the art. Two or more sequences can be compared by determining their "percent identity." The percent identity of two sequences, whether nucleic acid or amino acid sequences, is the number of exact matches between two aligned sequences divided by the length of the shorter sequences and multiplied by 100.

"Percent (%) amino acid sequence identity" with respect to proteins, polypeptides, antigenic protein fragments, antigens and epitopes described herein is defined as the percentage of amino acid residues in a candidate sequence that are identical with the amino acid residues in the reference sequence (i.e., the protein, polypeptide, antigenic protein fragment, antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The same applies to "percent (%) nucleotide sequence identity", mutatis mutandis.

For example, an appropriate alignment for nucleic acid sequences is provided by the local homology algorithm of Smith and Waterman, (1981), Advances in Applied Mathematics 2:482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), *Nucl. Acids Res.* 14(6):6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://wvw.ncbi.nlm.gov/cgi-bin/BLAST.

In some embodiments, the heterologous nucleic acid encodes antigenic domains or antigenic protein fragments rather than the entire antigenic protein. These fragments can be of any length sufficient to be antigenic or immunogenic. Fragments can be at least 8 amino acids long, preferably 10-20 amino acids, but can be longer, such as, e.g., at least 50, 100, 200, 500, 600, 800, 1000, 1200, 1600, 2000 amino acids long, or any length in between.

In some embodiments, at least one nucleic acid fragment encoding an antigenic protein fragment or immunogenic polypeptide thereof is inserted into the viral vector of the invention. In another embodiment, about 2-6 different nucleic acids encoding different antigenic proteins are inserted into one or more of the viral vectors. In some embodiments, multiple immunogenic fragments or subunits of various proteins can be used. For example, several different epitopes from different sites of a single protein or from different proteins of the same species, or from a protein ortholog from different species can be expressed from the vectors.

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

It must be noted that, as used herein, the singular forms "a", "an", and "the", include plural references unless the context clearly indicates otherwise. Thus, for example, reference to "an antigenic determinant" includes one or more antigenic determinants and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "affecting an immune response" includes the development, in a subject, of a humoral and/or a cellular immune response to a protein and/or polypeptide produced by the recombinant MVA and/or compositions and/or vaccines comprising the recombinant MVA of this invention A "humoral" immune response, as this term is well known in the art, refers to an immune response comprising antibodies, while the "cellular" immune response, as this term is well known in the art, refers to an immune response comprising T-lymphocytes and other white blood cells, especially the immunogen-specific response by HLA-restricted cytolytic T-cells, i.e., "CTLs." A cellular immune response occurs when the processed immunogens, i.e., peptide fragments, are displayed in conjunction with the major histocompatibility complex.

The term "substantially similar" in the context of the FMDV antigenic proteins of the invention indicates that a polypeptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "operably linked" means that the components described are in a relationship permitting them to function in their intended manner.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

As used herein, a "heterologous" gene, nucleic acid, antigen, or protein is understood to be a nucleic acid or amino acid sequence which is not present in the wild-type poxviral genome (e.g., MVA or MVA-BN). The skilled person understands that a "heterologous gene", when present in a poxvirus such as MVA or MVA-BN, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxvirus promoter.

The invention further comprises a complementary strand to a polynucleotide encoding an FMDV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component. The present invention relates to ovine, bovine, caprine and porcine vaccines or pharmaceutical or immunological compositions which may comprise an effective amount of a recombinant FMDV antigens and a pharmaceutically or veterinary acceptable carrier, excipient, or vehicle.

"Pharmaceutically acceptable carriers" are for example described in Remington's Pharmaceutical Sciences, by E. W. Martin, Mack Publishing Co., Easton, Pa., 15th Edition (1975). They describe compositions and formulations using conventional pharmaceutically acceptable carriers suitable for administration of the vectors and compositions disclosed herein. Generally the nature of the carrier used depends on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like, as a vehicle. For solid compositions (such as powders, pills, tablets, or capsules), conventional non-toxic solid carriers include, for example, pharmaceutical grades of mannitol, lactose, starch, or magnesium stearate. Pharmaceutical compositions can also contain minor amounts of non-toxic auxiliary substances such as wetting or emulsifying agents, preservatives, pH-buffering agents and the like such as, for example, sodium acetate or sorbitan monolaurate.

The term "prime-boost vaccination" refers to a vaccination strategy using a first, priming injection of a vaccine targeting a specific antigen followed at intervals by one or more boosting injections of the same vaccine. Prime-boost vaccination may be homologous or heterologous. A homologous prime-boost vaccination uses a vaccine comprising the same immunogen and vector for both the priming injection and the one or more boosting injections. A heterologous prime-boost vaccination uses a vaccine comprising the same immunogen for both the priming injection and the one or more boosting injections but different vectors for the priming injection and the one or more boosting injections. For example, a homologous prime-boost vaccination may use a recombinant MVA vector comprising the same nucleic acids expressing alphavirus antigens for both the priming injection and the one or more boosting injections. In contrast, a heterologous prime-boost vaccination may use a recombinant MVA vector comprising nucleic acids expressing one alphavirus protein for the priming injection and another recombinant MVA vector expressing a second one alphavirus protein not contained in the priming injection or vice versa. Heterologous prime-boost vaccination also encompasses various combinations such as, for example, use of a plasmid encoding an immunogen in the priming injection and use of a recombinant MVA encoding the same immunogen in the one or more boosting injections, or use of a recombinant protein immunogen in the priming injection and use of a recombinant MVA vector encoding the same protein immunogen in the one or more boosting injections.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semi-synthetic, or synthetic origin which either does not occur in nature or is linked to another polynucleotide in an arrangement not found in nature.

As used herein, "treat", "treating" or "treatment" of a disease means the prevention, reduction, amelioration, partial or complete alleviation, or cure of a disease e.g., an FMDV-caused disease. It can be one or more of reducing the severity of the disease, limiting or preventing development of symptoms characteristic of the disease being treated, inhibiting worsening of symptoms characteristic of the disease being treated, limiting or preventing recurrence of the disease in a subject who has previously had the disease, and limiting or preventing recurrence of symptoms in subjects.

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

FMDV Proteins

In one aspect, the present invention provides FMDV polypeptides from ovine, bovine, caprine, or porcine. In another aspect, the present invention provides a FMDV polypeptide and variant or fragment thereof.

Moreover, homologs of FMDV polypeptides from ovine, bovine, caprine, or porcine are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FMDV polypeptide can differ from the wild-type FMDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type FMDV or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the FMDV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for FMDV polypeptides, the DNA sequence of the FMDV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FMDV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FMDV polypeptide encoded by the nucleotide sequence is functionally unchanged.

3C Protease

During the maturation process, the FMDV protein P1 is cleaved by the protease 3C into three proteins known as VP0, VP1 and VP3 (or 1AB, 1D and 1C respectively; Belsham G. J., Progress in Biophysics and Molecular Biology, 1993, 60, 241-261). In the virion, the protein VP0 is then cleaved into two proteins, VP4 and VP2 (or 1A and 1B respectively).

High level expression of the 3C protease may lead to toxicity in the cells. The residual activity of 3C in the virus in eukaryotic cells is expected to be low although it is wt-3C, as the HIV frame shift upstream of the 3C coding sequence is expected to decrease translation by 20-fold, meaning equally lower amounts of 3C protein. In order to overcome the toxicity of high level expression of the 3C protease, the inventors of the present invention have found the following strategies. One strategy is to make mutations in the cDNA encoding FMDV 3C protease such that the expression levels of the 3C protease is decreased compared with expression levels of the 3C protease when un-mutated. Another strategy is to make mutations in the cDNA encoding FMDV 3C protease such that the activity level of the 3C protease is changed compared with expression level of the 3C protease when un-mutated.

According to a preferred embodiment, the cDNA encoding the 3C protease comprise the following mutations: C147T, C142L, and/or C31A/L47A.

Still another strategy is to clone the expression cassettes into a low copy-number-plasmid (pACYC177; e.g. commercially available at New England Biolabs). Still another strategy is to carefully choose the promoter responsible for lowering the expression level of the 3C protease. According to a preferred embodiment the expression level of the 3C protease is lowered by applying a weak promoter. The term "weak promoter" refers a promoter that weakens the expression level of the genes of interest.

Recombinant MVA

Provided herein are recombinant poxviruses (e.g., MVA or MVA-BN) comprising heterologous or foreign nucleic acid sequences derived from FMDV incorporated in a variety of insertion sites in the poxviral (e.g., MVA or MVA-BN) genome. The heterologous nucleic acids can encode one or more foreign proteins and/or foreign antigens including, for example, viral antigens.

Generally, a "recombinant" MVA as described herein refers to MVAs that are produced by standard genetic engineering methods, i.e., MVAs of the present invention are thus genetically engineered or genetically modified MVAs. The term "recombinant MVA" thus includes MVAs which have stably integrated recombinant nucleic acid, preferably in the form of a transcriptional unit, in their genome. A transcriptional unit may include a promoter, enhancer, terminator and/or silencer. Recombinant MVAs of the present invention may express heterologous antigenic determinants, polypeptides or proteins (antigens) upon induction of the regulatory elements.

As used herein, a "heterologous" gene, nucleic acid, antigen, or protein is understood to be a nucleic acid or amino acid sequence which is not present in the wild-type poxviral genome (e.g., MVA or MVA-BN). The skilled person understands that a "heterologous gene", when present in a poxvirus such as MVA or MVA-BN, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxviral promoter.

In one aspect, the present invention comprises a recombinant MVA vector comprising a heterologous nucleotide sequence encoding an antigenic determinant of a FMDV.

For the embodiments as described herein the FMDV may be derived from a virulent strain of FMDV, advantageously the FMDV 01 Manisa, 01 BFS or Campos, A24 Cruzeiro, Asia 1 Shamir, A Iran '96, A22 Iraq, SAT2 Saudi Arabia strains.

Still other strains may include FMDV strains A 10-61, A5, A 12, A24/Cruzeiro, C3/Indaial, 01, CI-Santa Pau, C1-C5, A22/550/Azerbaij an/65, SAT1-SAT3, A, A/TNC/71/94, A/IND/2/68, A/IND/3/77, A/IND/5/68, A/IND/7/82, A/IND/16/82, A/IND/17/77, A/IND/17/82, A/IND/19/76, A/TND/20/82, A/IND/22/82, A/IND/25/81, A/IND/26/82, A/IND/54/79, A/IND/57/79, A/TND/73/79, A/IND/85/79, A/IND/86/79, A/APA/25/84, A/APN/41/84, A/APS/44/05, A/APS/50/05, A/APS/55/05, A/APS/66/05, A/APS/68/05, A/BIM/46/95, A/GUM/33/84, A/ORS/66/84, A/ORS/75/88, A/TNAn/60/947/Asia/I, NIRN/05, Asia/IRN/05, O/HK/2001, O/UKG/3952/2001, O/UKG/4141/2001, Asia I/HNK/CHA/05 (GenBank accession number EF149010, herein incorporated by reference), Asia I/XJ (Li, ZhiYong et al. Chin Sci Bull, 2007), HK/70 (Chin Sci Bull, 2006, 51(17): 2072-2078), O/UKG/7039/2001, O/UKG/9161/2001, O/UKG/7299/2001, O/UKG/4014/2001, O/UKG/4998/2001, O/UKG/9443/2001, O/UKG/5470/2001, O/UKG/5681/2001, O/ES/2001, HKN/2002, 05India, O/BKF/2/92, K/37/84/A, KEN/1/76/A, GAM/51/98/A, A10/Holland, O/KEN/1/91, O/IND49/97, O/IND65/98, O/IND64/98, O/IND48/98, O/IND47/98, O/IND82/97, O/IND81/99, O/IND81/98, O/IND79/97, O/IND78/97, O/IND75/97, O/IND74/97, O/IND70/97, O/IND66/98, O/IND63/97, O/IND61/97, O/IND57/98, O/IND56/98, O/IND55/98, O/IND54/98, O/IND469/98, O/IND465/97, O/IND464/97, O/IND424/97, O/IND423/97, O/IND420/97, O/IND414/97, O/IND411/97, O/IND410/97, O/IND409/97, O/IND407/97, O/IND399/97, O/IND39/97, O/IND391/97, O/IND38/97, O/IND384/97, O/IND380/97, O/IND37/97, O/IND352/97, O/IND33/97, O/IND31/97, O/IND296/97, O/IND23/99, O/IND463/97, O/IND461/97, O/IND427/98, O/IND28/97, O/IND287/99, O/IND285/99, O/IND282/99, O/IND281/97, O/IND27/97, O/IND278/97, O/IND256/99, O/IND249/99, O/IND210/99, O/IND208/99, O/IND207/99, O/IND205/99, O/IND185/99, O/IND175/99, O/IND170/97, O/IND164/99, O/IND160/99, O/IND153/99, O/IND148/99, O/IND146/99, O/SKR 2000, A22/India/17/77.

Further details of these FMDV strains may be found on the European Bioinformatics Information (EMBL-EBI) web pages, and all of the associated nucleotide sequences are herein incorporated by reference. The inventors contemplate that all FMDV strains, both herein listed, and those yet to be identified, could be expressed according to the teachings of the present disclosure to produce, for example, effective vaccine compositions. Both homologous and heterologous strains are used for challenge to test the efficacy of the vaccines. The animal may be challenged intradermally, subcutaneously, spray, intra-nasally, intra-ocularly, intra-tracheally, and/or orally.

In another aspect, the present invention comprises a recombinant MVA vector comprising a heterologous nucleotide sequence encoding an antigenic determinant of a FMDV as described above, and further comprises heterologous nucleotide sequences encoding additional proteins required to form virus-like particles (VLPs).

Integration Sites into MVA

Heterologous nucleotide sequences encoding antigenic determinants of a FMDV may be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding antigenic determinants of a FMDV. The heterologous nucleotide sequences may, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding antigenic determinants of a FMDV.

The number of insertion sites of MVA comprising heterologous nucleotide sequences encoding antigenic determinants of a FMDV protein can be 1, 2, 3, 4, 5, 6, 7, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [J. Sambrook et al., Cold Spring Harbor Laboratory Press (1989)], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993)(see, e.g., Chapter 9: Expression of genes by Vaccinia virus vectors)] and Current Protocols in Molecular Biology [John Wiley & Son, Inc. (1998)(see, e.g., Chapter 16, Section IV: Expression of proteins in mammalian cells using vaccinia viral vector)].

For the generation of the various recombinant MVAs disclosed herein, different methods may be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

Expression of Heterologous FMDV Genes

In certain embodiments, expression of one, more, or all of the heterologous nucleotide sequences encoding antigenic determinants of a FMDV protein is under the control of one or more poxvirus promoters. In certain embodiments, the poxvirus promoter is a Pr7.5 promoter, a hybrid early/late promoter, a PrS promoter, a PrS5E promoter, a synthetic or natural early or late promoter, or a cowpox virus ATI promoter. In certain embodiments, the poxvirus promoter is selected from the group consisting of the PrS promoter (SEQ ID NO:1), the PrS5E promoter (SEQ ID NO:2), the Pr7.5 (SEQ ID NO:3), the PrLE1 promoter (SEQ ID NO:4), the Pr13.5 long promoter (SEQ ID NO:5) and the PrMVA095R promoter. Suitable promoters are further described in WO 2010/060632, WO 2010/102822, WO 2013/189611 and WO 2014/063832 incorporated fully by reference herewith.

A heterologous nucleotide sequence encoding an antigenic determinant of a FMDV protein can be expressed as a single transcriptional unit. For example, a heterologous nucleotide sequence encoding an antigenic determinant of a FMDV protein can be operably linked to a vaccinia virus promoter and/or linked to a vaccinia virus transcriptional terminator.

In certain embodiments, the "transcriptional unit" is inserted by itself into an insertion site in the MVA genome. In certain embodiments, the "transcriptional unit" is inserted with other transcriptional unit(s) into an insertion site in the MVA genome. The "transcriptional unit" is not naturally occurring (i.e., it is heterologous, exogenous or foreign) in the MVA genome and is capable of transcription in infected cells.

Preferably, the recombinant MVA comprises 1, 2, 3, 4, 5, or more transcriptional units inserted into the MVA genome. In certain embodiments, the recombinant MVA stably expresses heterologous nucleotide sequences encoding antigenic determinants of a filovirus protein encoded by 1, 2, 3, 4, 5, or more transcriptional units. In certain embodiments, the recombinant MVA comprises 2, 3, 4, 5, or more transcriptional units inserted into the MVA genome at 1, 2, 3, or more insertion sites in the MVA genome.

FMDV Vaccines and Pharmaceutical/Veterinary Compositions

Since the recombinant MVA viruses described herein are highly replication restricted and, thus, highly attenuated, they are ideal candidates for the treatment of a wide range of mammals including humans and even immune-compromised humans. Hence, provided herein are pharmaceutical/veterinary compositions and vaccines for inducing an immune response in a living animal body, including a human. Additionally provided is a recombinant MVA vector comprising a nucleotide sequence encoding an antigenic determinant of a FMDV protein for use in the treatment and/or prevention of a FMDV-caused disease.

The vaccine preferably comprises any of the recombinant MVA viruses described herein formulated in solution in a concentration range of $10^4$ to $10^9$ TCID$_{50}$/ml, $10^5$ to $5 \times 10^8$ TCID$_{50}$/ml, $10^6$ to $10^8$ TCID$_{50}$/ml, or $10^7$ to $10^8$ TCID$_{50}$/ml. A preferred vaccination dose for humans comprises between $10^6$ to $10^9$ TCID$_{50}$, including a dose of $10^6$ TCID$_{50}$, $10^7$ TCID$_{50}$, or $10^8$ TCID$_{50}$.

The pharmaceutical/veterinary compositions provided herein may generally include one or more pharmaceutically/veterinary acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the recombinant MVA viruses provided herein can be converted into a physiologically acceptable form. This can be done based on experience in the preparation of poxvirus vaccines used for vaccination against smallpox as described by H. Stickl et al., *Dtsch. med. Wschr.* 99:2386-2392 (1974).

For example, purified viruses can be stored at −80° C. with a titer of $5 \times 10^8$ TCID$_{50}$/ml formulated in about 10 mM Tris, 140 mM NaCl pH 7.4. For the preparation of vaccine shots, e.g., $10^2$-$10^8$ or $10^2$-$10^9$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between 4° C. and room temperature for several months. However, as long as no need exists, the ampoule is stored preferably at temperatures below −20° C.

For vaccination or therapy, the lyophilisate can be dissolved in an aqueous solution, preferably physiological saline or Tris buffer, and administered either systemically or locally, i.e., parenteral, subcutaneous, intravenous, intramuscular, intranasal, or any other path of administration known to the skilled practitioner. The mode of administration, the dose and the number of administrations can be optimized by those skilled in the art in a known manner.

Vaccines Using Homologous/Heterologous Prime-Boost Regimens

The vaccines and methods described herein may also be used as part of a homologous prime-boost regimen. In the homologous prime-boost, a first priming vaccination is given followed by one or more subsequent boosting vaccinations. The boosting vaccinations are configured to boost the immune response generated in the first vaccination by administration of the same recombinant poxvirus that was used in the first vaccination.

In one exemplary embodiment a homologous prime-boost regimen may be employed wherein a MVA viral vector as defined herein is administered in a first dosage. One or more subsequent administrations of an MVA viral vector as defined herein can be given to boost the immune response provided in the first administration. Preferably, the one or more antigenic determinants are the same or similar to those of the first administration The MVA recombinant viral vectors according to the present invention may also be used in heterologous prime-boost regimens in combination with another poxviral vector in which one or more of the initial prime vaccinations are done with either the MVA or the other poxviral vector as defined herein and one or more subsequent boosting vaccinations are done with the poxviral vector not used in the prime vaccination, e.g., if a MVA vector defined herein is given in a prime boost, then subsequent boosting vaccinations would be with the other poxviral vectors and vice versa.

Vaccines and Kits Comprising Recombinant MVA Viruses

Also provided herein are vaccines and kits comprising any one or more of the recombinant MVAs described herein. The kit can comprise one or multiple containers or vials of the recombinant MVA, together with instructions for the administration of the recombinant MVA to a subject at risk of FMDV infection. In certain embodiments, the instructions indicate that the recombinant MVA is administered to the subject in a single dose, or in multiple (i.e., 2, 3, 4, etc.) doses. In certain embodiments, the instructions indicate that the recombinant MVA virus is administered in a first (priming) and second (boosting) administration to naïve or non-naïve subjects. Preferably, a kit comprises at least two vials for prime/boost immunization comprising the recombinant MVAs as described herein for a first inoculation ("priming inoculation") in a first vial/container and for an at least second and/or third and/or further inoculation ("boosting inoculation") in a second and/or further vial/container.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

EXAMPLES

The detailed examples which follow are intended to contribute to a better understanding of the present invention. However, the invention is not limited by the examples. Other embodiments of the invention will be apparent to those skilled in the art from consideration of the specification and practice of the invention disclosed herein.

Example 1: Construction of Recombinant MVA

The following sections describe construction of two recombinant MVAs comprising one or more heterologous nucleic acids expressing an antigenic determinant of a FMDV protein. All other constructs described herein are made using similar methods.

1.1 Cloning and Generation of Two Recombinant MVA-BN®-FMDV Constructs

For the insertion of foreign genes into the MVA-BN® genome, BN has constructed a set of plasmids. These basic plasmids contain specific regions of the MVA-BN® genome covering deletion sites orintergenic regions of the MVA virus backbone, promoters and different selection cassettes. In order to clone a recombinant MVA-BN®-FMDV vaccine candidate, the transgenes were inserted into one of these basic plasmids, resulting in a final recombination plasmid which was used to promote the insertion of the transgenes into a specific site within the MVA genome via homologous recombination. To allow for homologous recombination between the plasmid and the MVA genome, primary CEF cells were infected with MVA-BN® and subsequently transfected with the respective recombination plasmids. During homologous recombination, flanking sequences of the plasmids recombine with the homologous sequences of the insertion sites in the MVA-BN® virus genome and target the plasmid sequences into the respective site. The presence of the selection cassettes within the inserted sequence allows for positive selection of recombinant MVA-BN® viruses. After initial amplification and 3-4 plaque purification steps under selective conditions, the recombinant product containing the FMDV-derived transgenes and the selection cassette was obtained. By further amplification and plaque purification steps under non-selective conditions, the selection cassette was excised and the final vaccine candidate was isolated. Final plaque purified clones were selected and amplified in 2-3 T175 tissue culture flasks to generate a Pre-Master virus stock which will be extensively characterized as described in section 1.2.

Two recombinant MVA-BN®-FMDV candidates in which the 3C protease was expressed in trans using separate promoters. 7 transgenes was inserted into one basic plasmid supporting homologous recombination into one of the well-established insertion sites of MVA-BN® described above.

Codon optimization of the nucleotide sequences in the proposed constructs involves the identification and removal of homologous sequences which could affect the stability of the construct and the optimization of the codon usage for the optimal expression of the transgenes in the respective host. This was performed in collaboration with a highly experienced CRO (GeneArt AG, Regensburg, Germany).

1.2 Genetic Analysis of Recombinant MVA-BN®-FMDV

Following generation of recombinant MVA-BN®-FMDV constructs by homologous recombination and plaque purifications, final clones were selected and amplified in T175 tissue culture flasks to generate a Pre-Master virus stock. The presence of the recombinant inserts, correct insertion into the targeted genome sites and absence of parental MVA-BN® virus in the Pre-Master virus stock was confirmed by Polymerase Chain Reaction (PCR) analysis. The correct sequence of the recombinant inserts was confirmed by sequence analysis. Sequencing was performed for the recombinant inserts including the flanking regions (more than 600 bp each, covering the sites of homologous recombination as contained in the recombination plasmids). A nested PCR was performed to verify the absence of the selection cassettes used during homologous recombination.

1.3 Analysis of Expression and Processing of Inserted FMDV Proteins

Following the generation of two viable MVA-BN®-FMDV viruses, their functionality were proven by analysis of their expressed recombinant proteins. The expression and processing of the FMDV proteins is essential for robust induction of immune response. BN will analyse expression and processing by Western blot and the ability of processed proteins to interact by co-immunoprecipitation assays. Further analysis of VLP formation was assessed by PIADC using electron microscopy. Based upon these analyses, 1.3.1 Expression and Processing of Antigens: Western Blot Western blotting for analysis of recombinant proteins expressed by MVA-BN® in various cell types was used for the detection of FMDV proteins with respect to their size and also for the relative estimation of expression levels from the respective recombinant MVA-BN® vectors. Depending on the nature of the FMDV-specific antibody, expression of native or denatured FMDV proteins can be detected. As antibodies specific for non-structural proteins as well as for virulent FMDV are commercially available only for serotype O1, BN recommends to use FMDV-antibodies (serotype A24) provided by PIADC. Concerning practical application, cells will be infected with MVA-BN®-FMDV at a defined MOI and harvested after 24 h. Cell extracts will be prepared and analysed by SDS-PAGE. The result of the assay will confirm expression of recombinant FMDV proteins and their correct size (indicative of correct processing).

1.3.2 Interaction of Proteins: IP-Western Blot

The interaction of structural proteins during the infectious cycle of FMDV is essential for the formation of infectious, highly immunogenic virus particles. Thus, the formation of non-infectious virus-like particles (VLPs) from MVA-BN® expressed FMDV proteins is desirable and requires specific protein Construction and Evaluation of Recombinant MVA-BN® FMDV Candidates Revised Statement of Work Example 2: Construction of Two Recombinant MVA-BN-FMDV Constructs (MVA-mBN360B and mBN361A)

The two constructs shown in FIG. 1 were generated as candidates for animal experiments. Construct #7B was selected as a candidate and production of MVB and FDP were performed. The recombinant MVA-BN constructs were generated as disclosed under heading 1.1 above.

A Master Virus Bank of construct #7B was produced in three roller bottles according to the SOPs at Bavarian Nordic. Cells were lysed and the product was aliquoted and stored for later use at −80° C. Genetic analysis for identity, purity and absence of empty vector and selection cassette was confirmed by PCR based methods and sequencing. Further a sterility test and a PCR based test for absence of *mycoplasma* were performed. The MVB of MVA-mBN360B (#7B) passed all tests. The titer of the MVB-material was determined to be $8.25 \times 10^6$ TCID$_{50}$/ml, which is regarded sufficient to go into BDS production.

The quality tests on the FDP material were finalized, including expression analysis (FIG. 2), co-IP (FIG. 3) titration, the later resulting in a titer of $1.47 \times 10^9$ TCID$_{50}$/ml.

Figure 2:
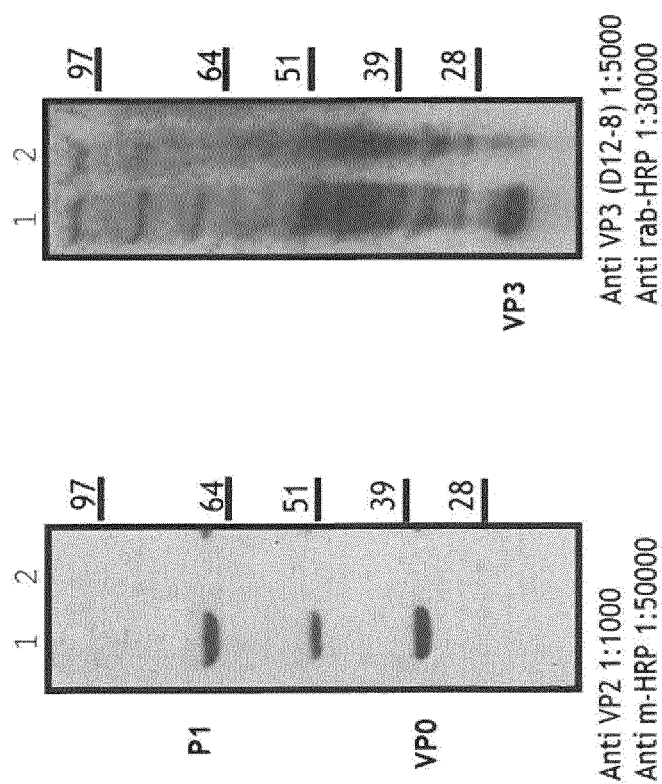
FIG. 2 shows expression and processing of the P1-2AB antigen with 3C protease activity.

The 3C protease and the P1-2AB are expressed by MVA-mBN360B (construct #7) in HeLa cells and lysates were applied to western blotting. The VP2 specific western shows, that P1 is processed to VP0, which is indicative for 3C protease activity, and the VP3 specific WB shows, that VP3 is efficiently released from the P1 precursor by 3C (FIG. 2).

Figure 3:
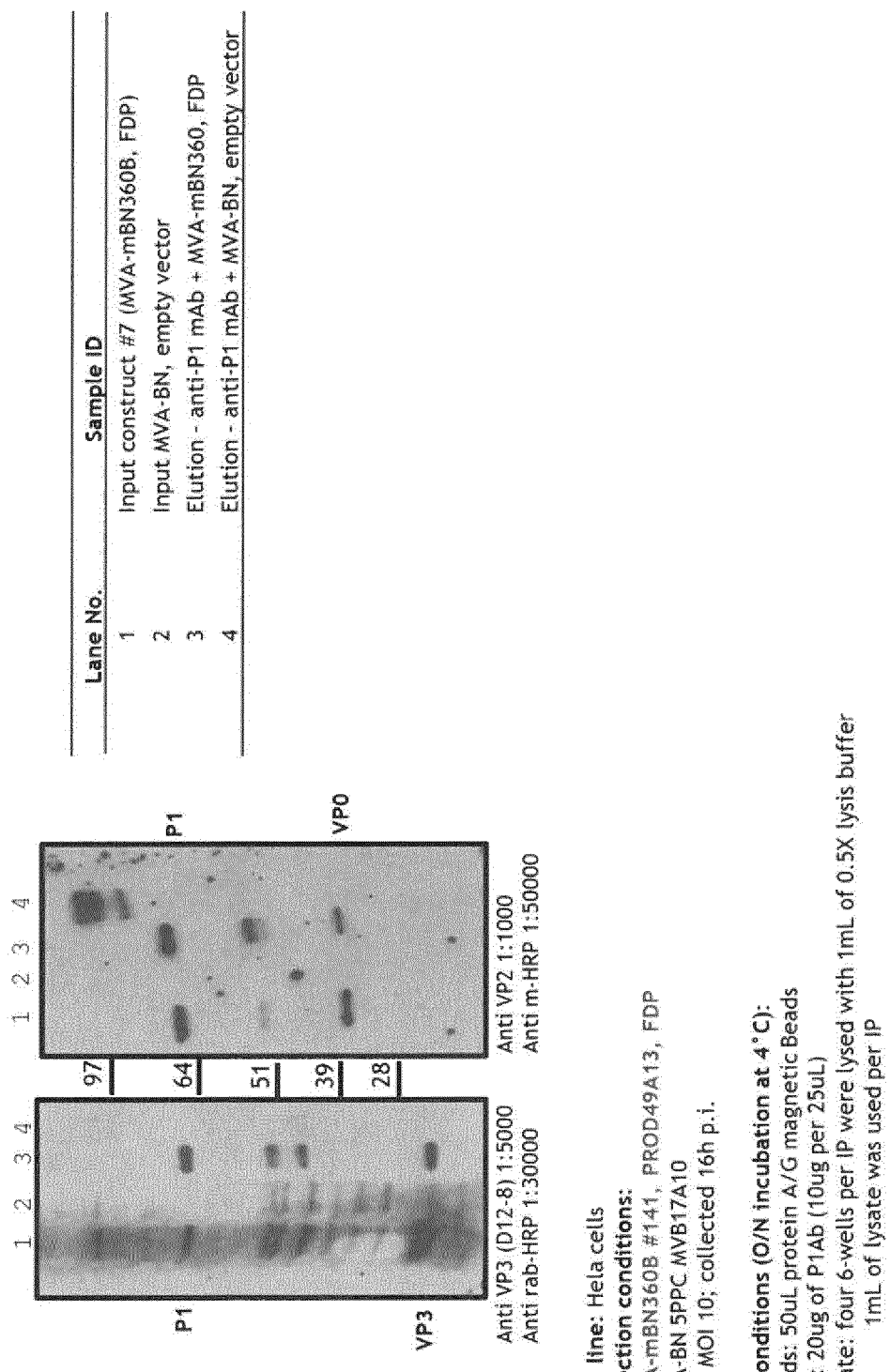
FIG. 3 shows co-IP of capsid material with correct conformation with a conformation specific anti-P1 antibody and detection of the co-precipitated antigens VP3 and VP0.

FDP material of MVA-BN360B construct #7 was applied to co-precipitation with a P1 conformation specific antibody. A VP3 specific band was detected with the VP3 antibody, which indicates interaction of VP3 single protein in a 'good' conformational structure of a capsid. The detection of a VP0 specific band with the VP2 antibody indicates interaction of P0 premature protein in a 'good' conformational structure (FIG. 3).

Example 3: MVA-BN-FMDV (MVA-mBN360B) in Cattle

Cattle were immunized on day 0 and on day 21 with doses of $10^9$ TCID$_{50}$ MVA-mBN360B. On day 4, animals were challenged with $10^4$ pfu of strain A24 Cruzeiro and analysed for signs of infection (tongue) and general disease as scored by the number of infected feet per animal.

TABLE 1

Disease scoring of cattle immunized or not with MVA-mBN360B vaccine.

| | | | Generalized Disease days post challenge[b] | | | |
|---|---|---|---|---|---|---|
| TG | Vaccine | ID | 3 | 7 | 10 | 14 |
| 01 | none | 1 | 2 | 4 | 4 | 4 |
| | | 2 | 2 | 3 | 3 | 3 |
| 02 | MVA-mBN360B | 3[a] | 0 | 0 | 0 | 0 |
| | | 4 | 0 | 0 | 0 | 0 |
| | | 5 | 0 | 0 | 0 | 0 |

All vaccinated animals were fully protected from a FMDV challenge, while none of the non-vaccinated animals were protected. [a] Animal without tongue lesion [b] Generalized Disease is given as the number of feet infected with FMDV (maximum score=4).

SEQ ID NO:6 [P1 amino acid sequence of FMDV strain A10, from U.S. Pat. No. 7,531,182]

SEQ ID NO:7 [3C amino acid sequence of FMDV strain A10, from U.S. Pat. No. 7,531,182]

DESCRIPTION OF THE SEQUENCE LISTING

SEQ ID NO:1 [DNA sequence of PrS promoter]
SEQ ID NO:2 [DNA sequence of PrS5E promoter: 1x (PrS)+5x (Pr7.5e)]
SEQ ID NO:3 [DNA sequence of Pr7.5 promoter]
SEQ ID NO:4 [DNA sequence of PrLE1 promoter—5X-ATI+Pr7.5e]
SEQ ID NO:5 [Pr13.5 promoter sequence]

The invention claimed is:

1. A vaccine that elicits a protective immune response to FMDV when administered to cattle and that comprises:
   (a) a recombinant MVA comprising:
   (i) a first transcriptional unit that is inserted into the intergenic region IGR 88/89 of the MVA and that comprises a nucleotide sequence encoding the foot-and-mouth disease virus (FMDV) P1 region operably linked to a promoter that is Pr13.5-long; and
   (ii) a second transcriptional unit that is inserted into the intergenic region IGR 64/65 of the MVA and that comprises a nucleotide sequence encoding FMDV 3C protease downstream from an HIV frameshift and operably linked to a weak promoter that is PrMVA095R, wherein the 3C protease comprises the mutation C142T; and
   (b) a pharmaceutical or veterinary acceptable carrier, excipient, or vehicle;
wherein said protective immune response prevents the development of FMDV-caused lesions in said cattle.

2. The recombinant MVA of claim 1, wherein the amino acid sequence of the encoded FMDV P1 region shares at least 90% sequence identity with the amino acid sequence set forth in SEQ ID NO:6 and the amino acid sequence of the encoded FMDV 3C protease shares at least 90% sequence identity with the amino acid sequence set forth in SEQ ID NO:7.

3. The recombinant MVA of claim 1, wherein the MVA is an MVA-BN virus or derivative of MVA-BN having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

4. The recombinant MVA of claim 1, wherein the MVA is MVA-BN as deposited at the European Collection of Animal Cell cultures (ECACC) under accession number V00083008.

5. The vaccine of claim 1, wherein the protective immune response against foot-and-mouth disease virus (FMDV) prevents the development of FMDV-caused tongue lesions when an effective amount of the vaccine is administered to cattle.

6. A method of inducing a protective immune response against FMDV in an animal, the method comprising the step of administering to the animal a vaccine comprising an effective amount of a recombinant Modified Vaccinia virus Ankara (MVA) comprising:
   (i) a first transcriptional unit that is inserted into the intergenic region IGR 88/89 of the MVA and that comprises a nucleotide sequence encoding the foot-and-mouth disease virus (FMDV) P1 region operably linked to a promoter that is Pr13.5-long; and
   (ii) a second transcriptional unit that is inserted into the intergenic region IGR 64/65 of the MVA and that comprises a nucleotide sequence encoding the FMDV 3C protease downstream from an HIV frameshift and operably linked to a weak promoter that is PrMVA095R, wherein the 3C protease comprises the mutation C142T, whereby said protective immune response prevents the development of FMDV-caused lesions in the animal.

7. The method of claim 6, wherein the amino acid sequence of the encoded FMDV P1 region shares at least 90% sequence identity with the amino acid sequence set forth in SEQ ID NO:6 and the amino acid sequence of the encoded FMDV 3C protease shares at least 90% sequence identity with the amino acid sequence set forth in SEQ ID NO:7.

8. The method of claim 6, wherein the animal is a bovine.

9. The method of claim 6, wherein the MVA is an MVA-BN virus or derivative of MVA-BN having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

10. The method of claim 6, wherein the MVA is MVA-BN as deposited at the European Collection of Animal Cell cultures (ECACC) under accession number V00083008.

* * * * *